(12) United States Patent  (10) Patent No.: US 7,815,857 B2
Dechant et al.  (45) Date of Patent: Oct. 19, 2010

(54) DEVICE FOR TAKING-UP AND STUDYING OR MANIPULATING A SAMPLE LIQUID IN A MICROFLUIDIC PLATFORM

(75) Inventors: Christian Dechant, Bochum (DE); Klaus Kadel, Witten (DE); Gert Blankenstein, Dortmund (DE)

(73) Assignee: Boehringer Ingelheim microParts GmbH, Dortmund (DE)

( * ) Notice: Subject to any disclaimer, the term of this patent is extended or adjusted under 35 U.S.C. 154(b) by 1069 days.

(21) Appl. No.: 11/247,584

(22) Filed: Oct. 12, 2005

(65) Prior Publication Data

US 2006/0078469 A1   Apr. 13, 2006

(30) Foreign Application Priority Data

Oct. 13, 2004   (DE)   ................ 10 2004 050 062

(51) Int. Cl.
*B01L 3/00*   (2006.01)
(52) U.S. Cl. ............... 422/61; 422/58; 422/60; 422/68.1; 422/100; 422/102; 422/103; 422/104
(58) Field of Classification Search ............. 422/58, 422/60, 61, 63, 66, 68.1, 99, 100, 102–104; 204/403.01
See application file for complete search history.

(56) References Cited

U.S. PATENT DOCUMENTS

| | | | |
|---|---|---|---|
| 5,514,152 A | 5/1996 | Smith | |
| 5,609,823 A | 3/1997 | Harttig et al. | |
| 5,679,311 A | 10/1997 | Harttig et al. | |
| 6,207,000 B1 | 3/2001 | Schwobel et al. | |
| 6,375,871 B1 | 4/2002 | Bentsen et al. | |
| 6,562,210 B1 | 5/2003 | Bhullar et al. | |
| 6,761,962 B2 | 7/2004 | Bentsen et al. | |
| 2003/0024811 A1 | 2/2003 | Davies et al. | |
| 2004/0086871 A1* | 5/2004 | Schembri | ............. 435/6 |
| 2005/0079104 A1 | 4/2005 | Polwart et al. | |
| 2005/0089449 A1 | 4/2005 | Polwart et al. | |
| 2005/0230253 A1 | 10/2005 | Marquant | |

FOREIGN PATENT DOCUMENTS

| | | |
|---|---|---|
| CA | 2 500 071 A1 | 4/2004 |
| WO | WO 03/045557 A2 | 6/2003 |

\* cited by examiner

*Primary Examiner*—Jill Warden
*Assistant Examiner*—Dean Kwak
(74) *Attorney, Agent, or Firm*—Roberts Mlotkowski Safran & Cole, P.C.; David S. Safran

(57) ABSTRACT

A device and a plurality of microfluidic platforms for taking up and especially studying or manipulating a sample liquid, a measuring instrument for use with the device and platforms, and a process for performing the studying or manipulating of the sample liquid. Very simple, hygienic and user-friendly handling is enabled in that the platforms which are connected to one another in a sealed state and can each be individually separated and individually, preferably simultaneously, opened for taking up of a sample, such as blood, for, e.g., performing a glucose determination.

13 Claims, 6 Drawing Sheets

DEVICE FOR TAKING-UP AND STUDYING OR MANIPULATING A SAMPLE LIQUID IN A MICROFLUIDIC PLATFORM

BACKGROUND OF THE INVENTION

1. Field of Invention

This invention relates to a device with a plurality of microfluidic platforms for taking-up and especially studying or manipulating a sample liquid, a measuring instrument for studying a sample liquid, for example, blood for glucose determination, and a process for studying or manipulating a sample liquid.

The concept of a "microfluidic platform"—hereinafter often abbreviated "platform"—in this invention, comprises a sample carrier, test strip or the like, which can take up a sample liquid to be manipulated or studied especially by capillary forces. In particular, the platforms are used to perform individual tests or to take measurements, for example, glucose determination of blood. However, the platforms can also be used for any other study, especially of the bodily fluids of humans or animals as a sample liquid. To study or manipulate a sample liquid, the platforms have especially reagents, filters or the like for the sample liquid. The platforms are ordinarily sealed for keeping or storing.

2. Description of Related Art

Microfluidic platforms are used, for example, in the form of test strips for determination of the blood sugar level (glucose determination). To date, it has been necessary to remove an individual test strip from a dispenser package and wet it with blood as the sample liquid which is then taken up by the test strip. Then, the test strip must be inserted manually into a corresponding measurement or test device which, first of all, indicates whether blood has been taken up in a sufficient amount and finally determines the glucose value. Thereafter, the test strip must be removed again and discarded. The described sequence is complex and associated with specific uncertainties. Handling of the comparatively small test strip is especially difficult for an unpracticed user. There is the risk of unwanted contamination. Furthermore, often blood is not taken up in a sufficient amount; however, this can only be ascertained after insertion of the test strip into the measuring instrument, so that the same procedure must then be repeated.

International Patent Application Publication WO 03/045557 A2 (corresponding to U.S. Patent Application Publications 2005089449 A1 and 2005079104 A1), which forms the starting point of this invention, discloses a band-like arrangement of a plurality of platforms which can be used in succession for a plurality of automated studies or manipulations of sample liquids which directly follow one another. But the known arrangement is not intended or suited for individual study or manipulation of a sample liquid.

SUMMARY OF THE INVENTION

A primary object of this invention is to devise a device with a plurality of microfluidic platforms for taking up and studying or manipulating sample liquids, a measuring instrument for studying a sample liquid by means of a microfluidic platform, and a process for studying or manipulating a sample liquid by means of a microfluidic platform, individual take-up, and especially study or manipulation, of the sample liquid as required. Therefore, preferably, individual studies or manipulations are enabled independently of previous studies and manipulations, and especially for hygienic reasons, each platform used can be discarded immediately after its use, independently of the other platforms.

One aspect of this invention is to individually separate and individually open the platforms for a plurality of platforms which are present, especially in a belt-shaped, for example, wound or stacked arrangement, so that the platforms can be used individually for taking up and especially studying or manipulating a sample liquid as required, and then, can be discarded independently of the platforms which have not yet been used. This enables much simplified handling for a user who must, for example, check his or her blood sugar level at certain time intervals. In accordance with the invention, it is then possible to use a measuring instrument which contains a plurality of platforms and which allows determination of the blood sugar value (glucose determination) as required without the user's having to first insert an individual test strip into the measuring instrument after taking up blood and then removing it again. Rather the measuring instrument after preferably automated opening of a platform can be used directly to take up blood, and for example, to determine the glucose value, and immediately after determination, the used platform can be directly output and discarded. This enables optimum hygienic use with simple handing as required.

Especially preferably, the individual platforms are each necessarily opened by separation for taking up the sample liquid. This allows very simple handing and use of the individual platforms.

Other advantages, features, properties and aspects of this invention will be apparent from the following description of preferred embodiments together with the accompanying drawings.

DETAILED DESCRIPTION OF THE INVENTION

In the figures, the same reference numbers are used for the same or similar parts, corresponding or comparable properties and advantages being achieved even if a repeated description is omitted.

Figure 1:
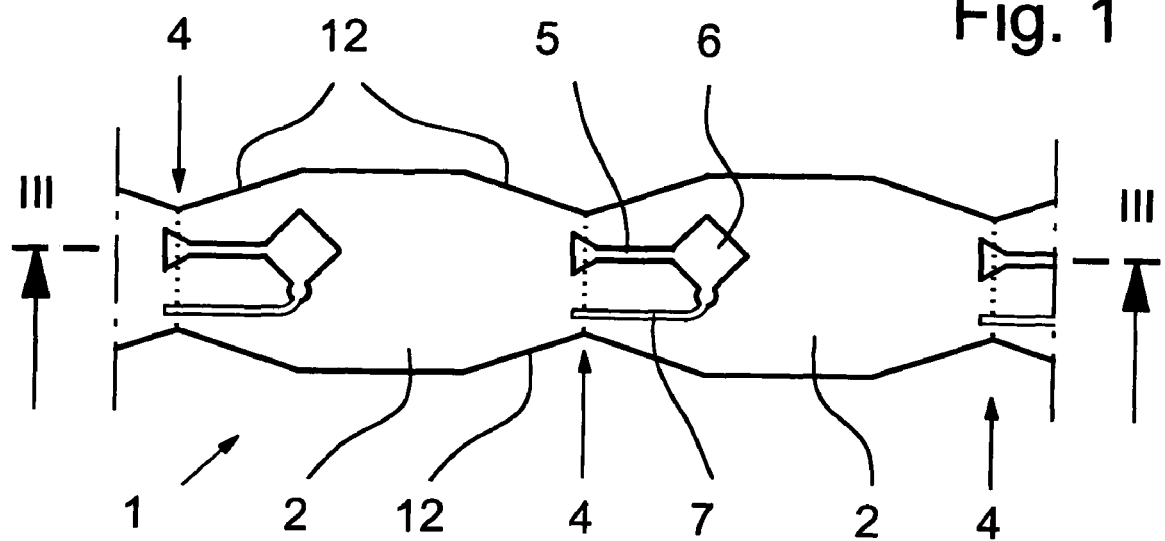
FIG. 1 shows an extract top view of a device according to the invention with a plurality of platforms according to a first embodiment.

FIG. 1 shows a device 1 according to a first embodiment of the invention with a plurality of microfluidic platforms 2 in the initially described sense. The platforms 2 are used especially to take up and study or manipulate a sample liquid 3, for example, blood for glucose determination. As is shown in FIG. 2, for example, a separated platform 2 has taken up the sample liquid 3 (blood) from a finger F.

Figure 2:
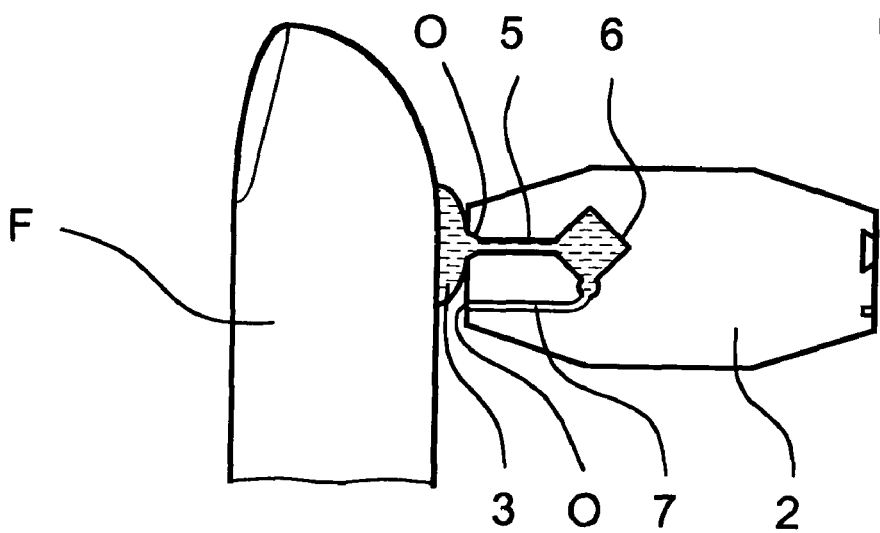
FIG. 2 schematically shows a separated platform of the device according to the first embodiment when the sample liquid is being taken up.
Figure 3:
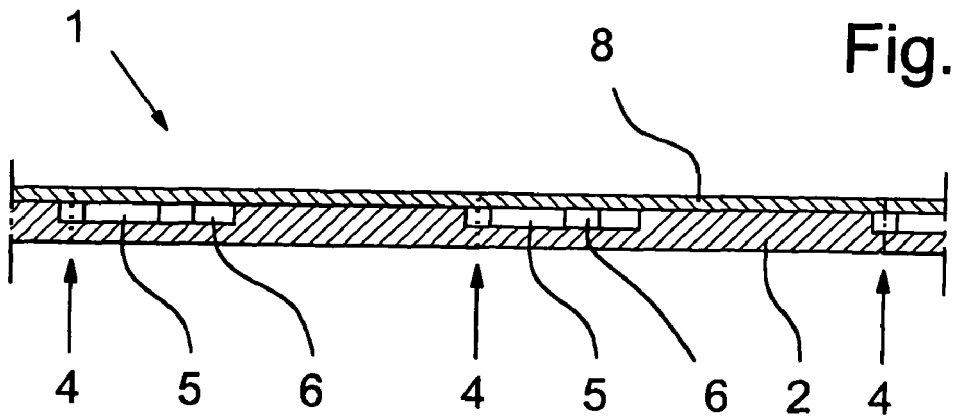
FIG. 3 is a sectional view taken along line III-III in FIG. 1.

In the first embodiment of the device 1 which is shown in FIGS. 1 to 3, the platforms 2, in the unused and sealed state, are directly connected to one another via the frangible connections 4 shown by the broken line. These connections 4 are preferably made by scoring.

Each platform 2 preferably has a take-up channel 5 for taking up the sample liquid 3, a following sample chamber 6 which is used especially to study and/or manipulate the sample liquid 3—if necessary under the action of a reagent (not shown), which is especially dried, and which is added beforehand to the sample chamber 6—and if necessary, a vent channel 7 which adjoins the sample chamber 6. Preferably at the output of the sample chamber 6 toward the vent channel 7, a liquid stop is formed so that the sample liquid 3 which is flowing into the take-up channel 5 and the sample chamber 6, preferably only by capillary forces, is not sucked or otherwise caused to enter into the ventilation channel 7, as is indicated in FIG. 2.

It can be taken from the section as shown in FIG. 3 that the cavities of the platforms 2, such as the take-up channel 5, the sample chamber 6 and the ventilation channel 7, are made preferably in a suitable material, preferably plastic or optionally glass, so as to be open to the top, being closed on the top side by a covering 8. The covering 8, in the illustrated example, is made preferably continuous in the direction in which the strip runs, and is optionally also provided with scoring according to the connections 4.

The covering 8 is preferably made of a film. However, it can also be made of any other suitable material. Preferably, the cover 8 is laminated, welded, cemented or in some other way connected to the plate-shaped material which forms the cavities of the platforms 2 in order to ensure the preferably desired hermetic sealing of the cavities.

In the first embodiment, the take-up channel 5 and the vent channel 7 extend beyond the connection 4 only partially into the following platform 2. In this way, when the platforms 2 are still joined to one another, the take-up channels 5 and vent channels 7 are closed, and the individual platforms 2, therefore, are not yet opened for taking up the sample liquid 3.

The aforementioned execution leads to the platforms 2 being individually separable and individually openable. In particular, for the first embodiment, the individual platforms 2 are each necessarily opened by separation—therefore detachment in the area of the connection 4—for taking up the sample liquid 3 since, in this way, the corresponding take-up channel 5 and vent channel 7 are provided with openings O. Then, each platform 2 is ready individually for taking up the sample liquid 3, as shown in FIG. 2, and for subsequent study and manipulation of the sample liquid 3 in the sample chamber 6.

The platforms 2, depending on the requirement and execution, can be easily separated from one another as required, for example, by cutting, breaking or tearing in the area of their connections 4. The selective separation of the individual platforms can be performed manually, or especially using a suitable means, and the scoring which is preferably provided is not absolutely necessary, especially if a severing or cutting mechanism is to be utilized.

Figure 4:
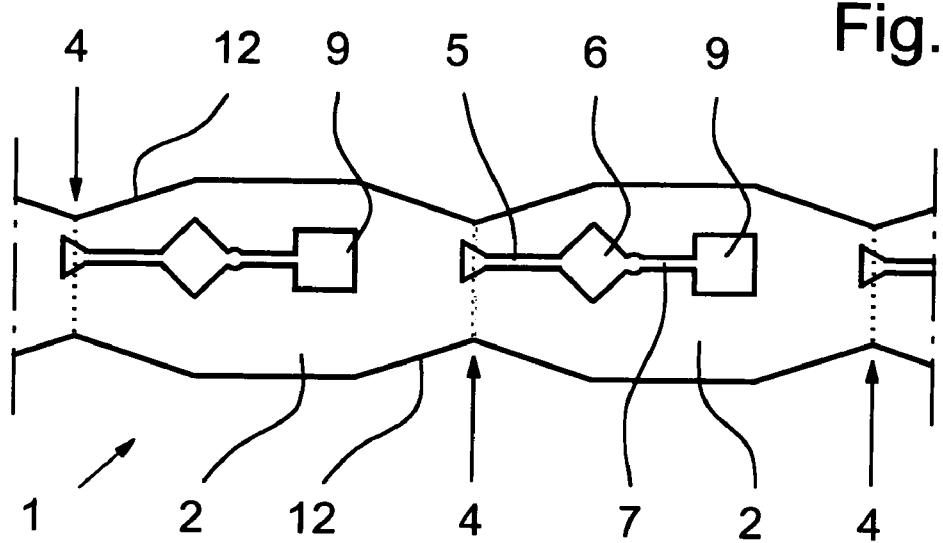
FIG. 4 shows an extract top view of a device according to the invention with a plurality of platforms according to a second embodiment.

FIG. 4 shows a second embodiment of the device 1 in which the plate elements 2 have been only somewhat modified in comparison to the first embodiment. In the second embodiment, the vent channel 7 leads to an otherwise closed vent chamber 9. The vent chamber 9 has a volume which is selected to be large enough that, when the take-up channel 5 is opened, the sample liquid 3 can flow into the sample chamber 6 and can displace the air contained in it via the vent channel 7 into the vent chamber 9. Therefore, it is unnecessary to open the vent for taking up the liquid 3 in the second embodiment.

Figure 5:
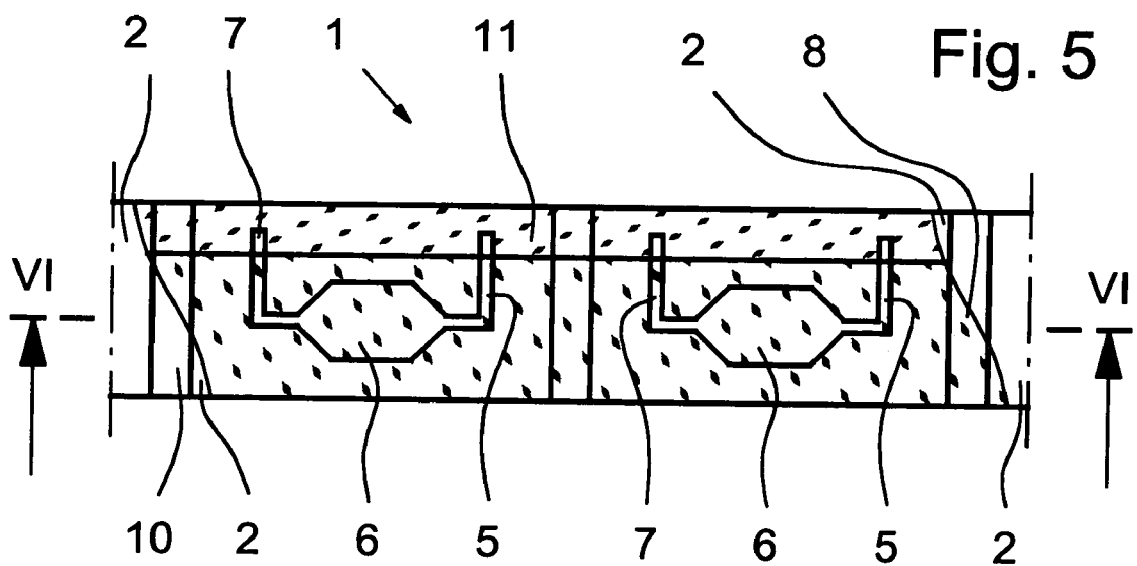
FIG. 5 shows an extract top view of a device according to a third embodiment of the invention.
Figure 6:
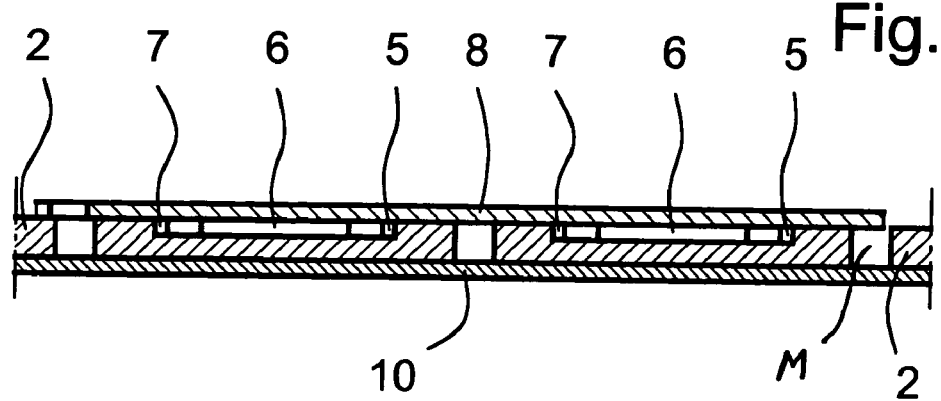
FIG. 6 is a sectional view taken along line VI-VI from FIG. 5.

FIGS. 5 & 6 show a third embodiment of the device 1 according to the invention with a plurality of platforms 2; FIG. 5 shows the platforms 2 in an extract top view and FIG. 6 shows them in an extract side view.

In the third embodiment, the platforms 2, which are made selectively stiff or flexible, cannot be directly joined to one another, but are located on a common carrier 10 which is made preferably band-like and is used especially at the same time as a transport or conveyor belt. In this embodiment, the platforms 2 are also arranged preferably in succession, at least essentially in a band-like manner.

In the third embodiment the cavities, especially of the take-up channel 5 and the vent channel 7, run preferably exclusively in the respective platform 2 and do not extend into the adjacent platform 2. Instead, the two channels 5, 7 preferably end in the area of the lengthwise edge within the respective platform 2. In the third embodiment, the sample chamber 6 is located at least essentially in between these channels, but in other areas than the lengthwise side at which the channels 5, 7, end, such as in the middle of the respective platform 2.

The platforms 2 are in turn covered by a covering 8, which is made continuous in the illustrated sample. However, if necessary, the covering 8 can also be formed from separate pieces which are assigned to the individual platforms 2.

The covering 8, again, is preferably made of a film or other suitable material. In particular, the covering 8 covers all cavities, such as the take-up channel 5, the sample chamber 6 and the vent channel 7, of each individual platform 2 in the closed state. In the illustrated example, the covering 8 encompasses a separately detachable or openable area which is made preferably as a continuous lengthwise strip 11 in order to enable opening of the individual platforms 2 for taking up a sample liquid 3, especially at least the take-up channels 5.

Figure 7:
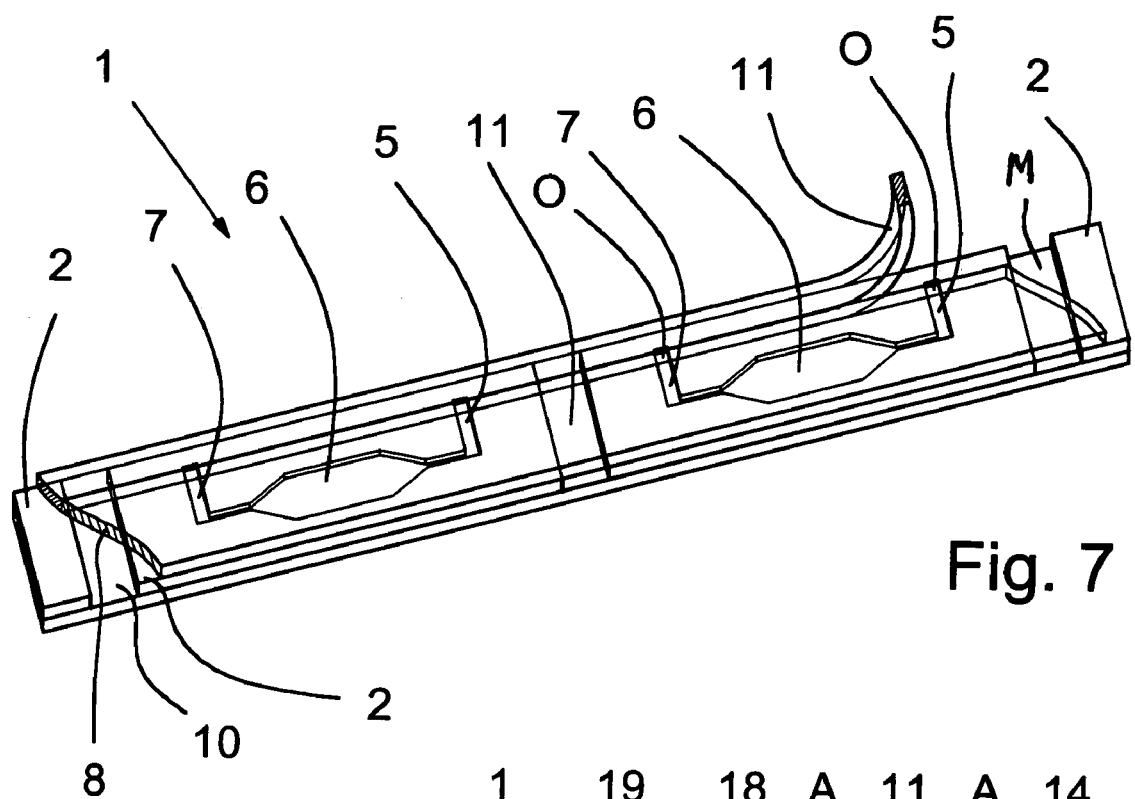
FIG. 7 is a perspective view of the device according to the third embodiment when a platform is opened.

In the third embodiment, the covering 8 is made at least partially, especially with respect to the strip 11, such that it can be detached from the platforms 2 in order to be able to individually open the platforms 2 by providing their take-up channel 5 and vent channel 7 with openings O, but without completely uncovering the take-up channel 5 and the vent channel 7, and without uncovering the sample chamber 6, as is shown schematically in FIG. 7. Thus, the desired functionality of the individual platforms 2 for taking up and studying or manipulating the sample liquid 3 is preserved.

In order to enable simple separation of the platform 2 from the carrier 10, the platforms 2 can be raised and especially removed individually from the carrier 10. Preferably, there is a correspondingly detachable cement connection between the platforms 2 and the carrier 10.

Alternatively, the carrier 10 can also be produced from the same material as the platforms 2 and optionally even integrally with them.

The device 1 according to the first, second or third embodiment is preferably made such that it or the not yet separated platforms 2 can be wound or stacked, especially as a result of the inherent flexibility of the platforms 2 and/or of the carrier 10 and/or as a result of the correspondingly flexible connections 4.

The device 1 and the platforms 2 are preferably provided with mechanical and/or optical markings, recesses, holes, weakenings, tapers 12 (FIGS. 1 & 4) or notches 13 (FIG. 10) in order to enable or facilitate conveyance, positioning, grasping and/or separation of individual platforms 2. In this regard, if the covering 8 is transparent, then the spaces between the platforms 2 (see, M in FIGS. 6 & 7) can, themselves, serve as the optical markings.

First of all, a first embodiment of a measuring instrument 14 according to the invention for use with the third embodiment of the device 1 is explained in detail below using FIGS. 8 & 9, before a fourth embodiment of the device 1 is explained.

The measuring instrument 14 is used to hold several, preferably single-use platforms 2, especially a device 1 with several platforms 2, shown here as a coil of numerous platforms. The measuring instrument 14 preferably has an interchangeable magazine 15 for holding and storing the device 1 and the platforms 2.

The measuring instrument 14 has a conveyor means or advance means 16 for conveyance of the platforms 2. In the illustrated embodiment, the measuring instrument 14 is made to hold the device 1 according to the third embodiment. The carrier 10 is used especially in the manner of a conveyor belt with, for example, a star wheel or gear wheel (not shown) being used for producing a defined advance and positioning of the carrier 10, and thus, of the platforms 2. Driving can take place, for example, mechanically or electrically, especially by means of a stepping motor or the like. In the illustrated embodiment, the advance device 16 rolls up the carrier 10 which is optionally guided around a guide roller 17 as necessary and both the carrier 10 and strip 11 are advanced manually by actuating levers A.

The measuring instrument 14 furthermore has an opening means 18 for individual opening of the platforms 2 for taking up the sample liquid 3. In the illustrated example, this takes place by pulling the strip 11 off the platform 2 which is to be opened. Preferably, the strip 11 of the covering 8 is guided over a guide roller 19 and is rolled up directly by the opening means 18.

Figure 8:
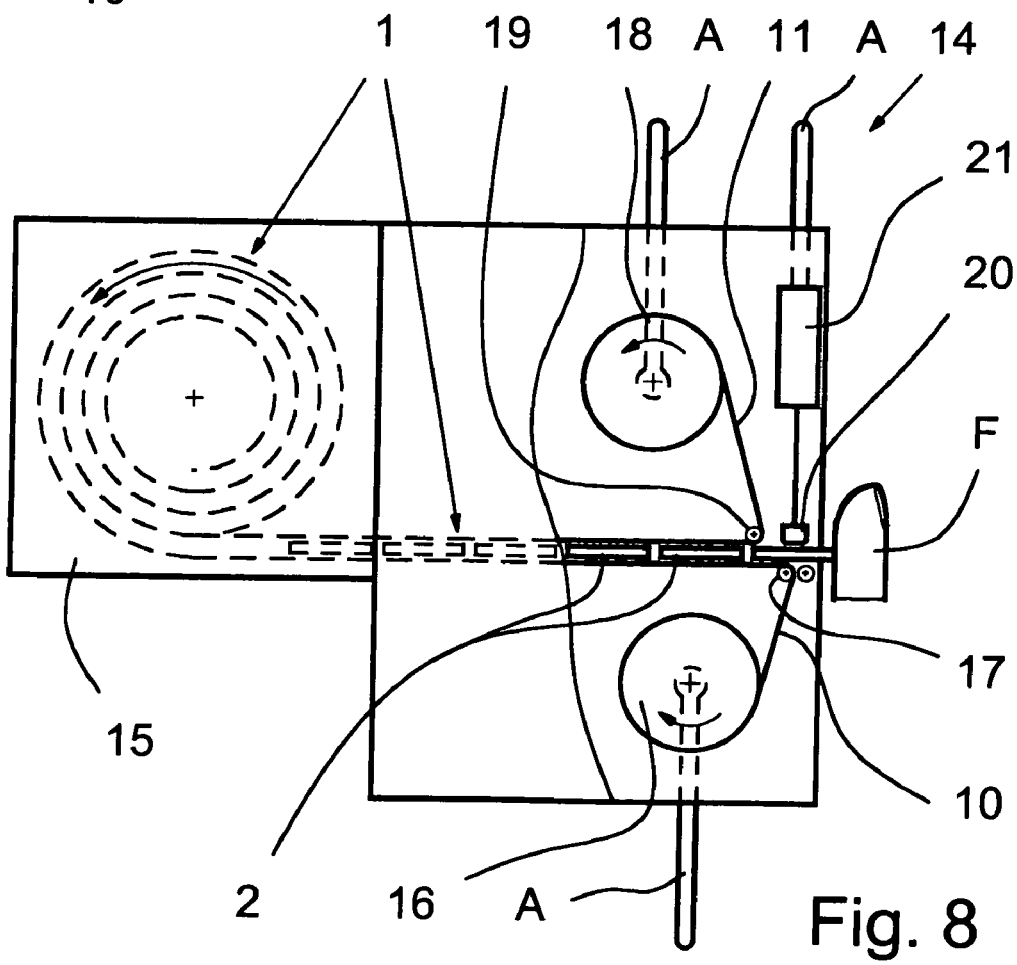
FIG. 8 is a schematic view of a first embodiment of a measuring instrument according to the invention with the third embodiment of the device while the sample liquid is being taken up.
Figure 9:
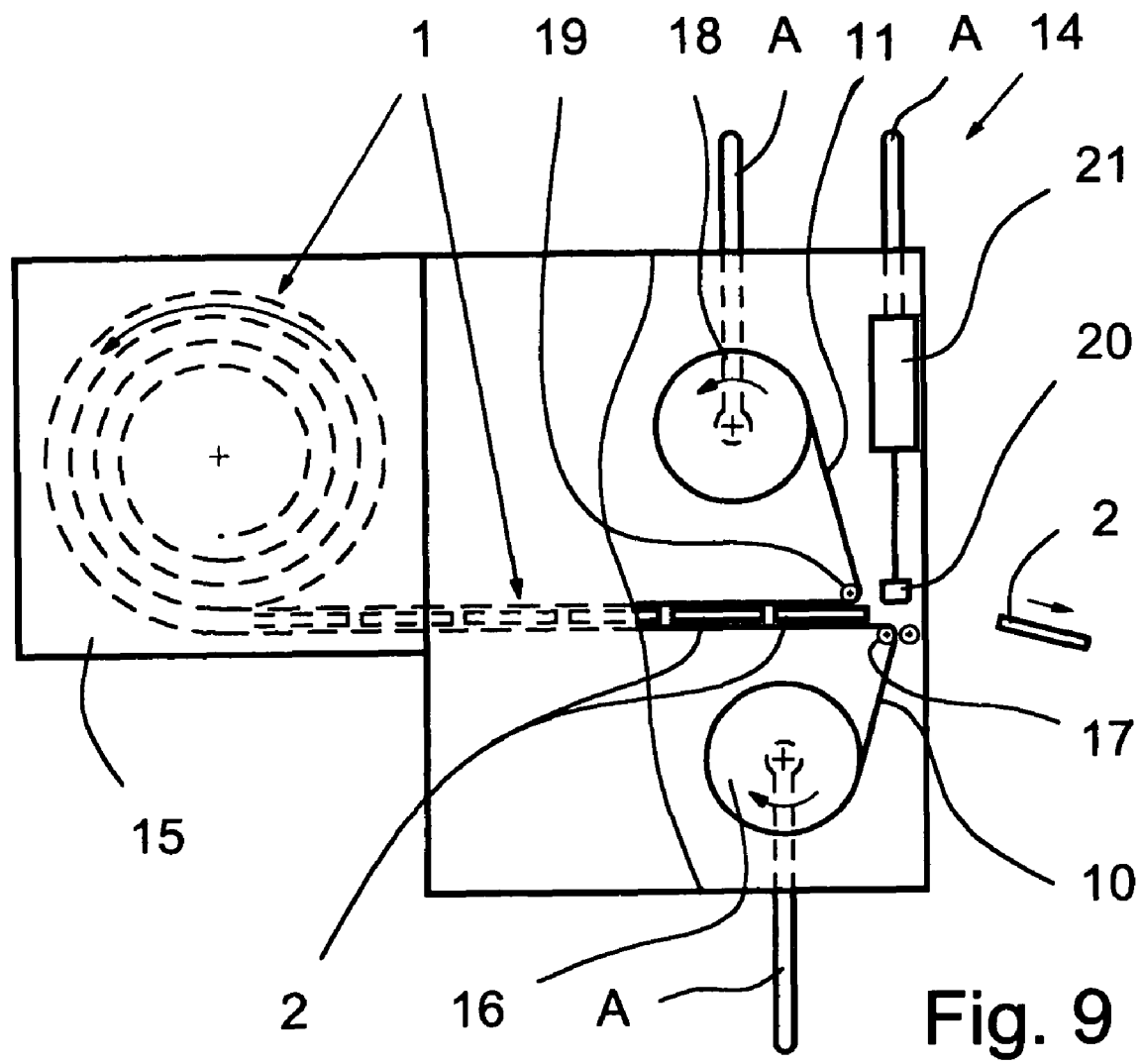
FIG. 9 shows the measuring instrument according to the first embodiment when a used platform is being ejected.

In the illustrated embodiment, the opened platform 2 is already conveyed into an advanced position in which the platform 2 projects at least with an area which contains the take-up channel 5 out of the measuring instrument 14 or is exposed, so that then the sample liquid 3 can be taken up, as is shown in FIG. 8, for example, by the finger F. Therefore, direct manual handling of the platform 2 for taking up the sample liquid 3 is not necessary. Rather, the opened platform 2 can be reliably held by a user by means of the measuring instrument 14.

After taking up the sample liquid 3, for example, blood, the sample liquid 3 is studied or manipulated. For example, the sample liquid 3 as a result of capillary forces flows into the sample chamber 6 and interacts there, preferably with a reagent which is added beforehand, such that, in particular, the desired measurement or determination, such as the glucose determination, can take place by the measuring instrument 14, for example, by a suitable optical method. To do this, the measuring instrument 14 preferably has a corresponding measurement means 20, such as an optical detector or sensor, and a display means 21 for displaying the determined value.

Then, the used platform is (completely) separated from the carrier 10 and ejected. The measuring instrument 14 can have a corresponding separating means and ejection means for this purpose. In the illustrated embodiment, this is achieved simply by continuing to convey the carrier 10 beyond the position shown in FIG. 8, as is shown in FIG. 9.

It should be noted that the separation of the used platform 2, or the one to be used, from the carrier 10, or for example, from the following platform 2, can take place selectively immediately before, simultaneously with, or after opening of the platform 2 for taking up the sample liquid 3 and/or taking up and/or studying the sample liquid 3 in the respective platform 2.

The measuring instrument 14 is made to be preferably mobile, especially portable. In order to enable a manageable, light device, the means which act mechanically on the device 1 or the individual platforms 2 are reached or driven preferably only by manual actuation.

Figure 10:
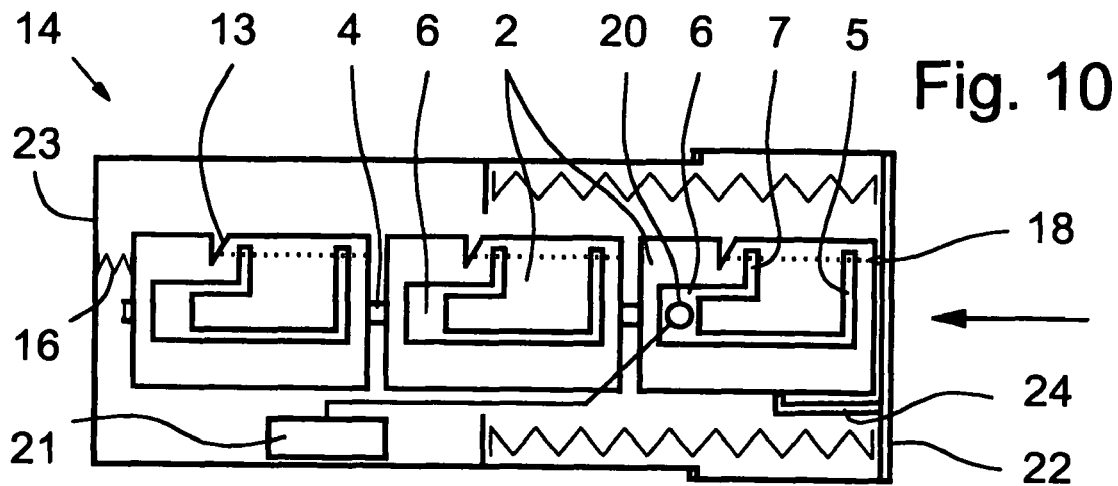
FIG. 10 is a schematic representation of a second embodiment of a measuring instrument according to the invention with a fourth embodiment of the device according to the invention.
Figure 11:
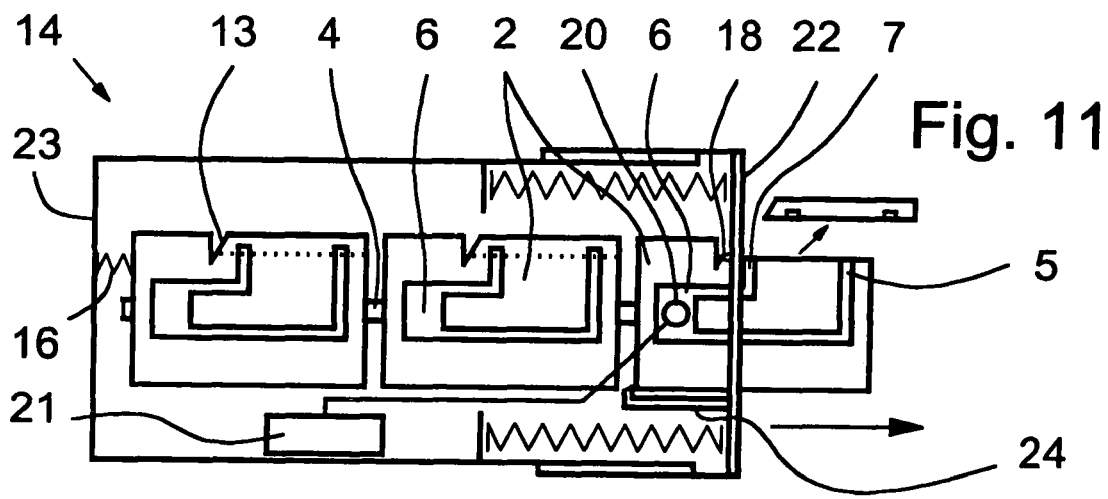
FIG. 11 shows the measuring instrument according to the second embodiment with a platform opened for taking up the sample liquid, a portion of the platform that has been removed to open it being shown discharged from the instrument.
Figure 12:
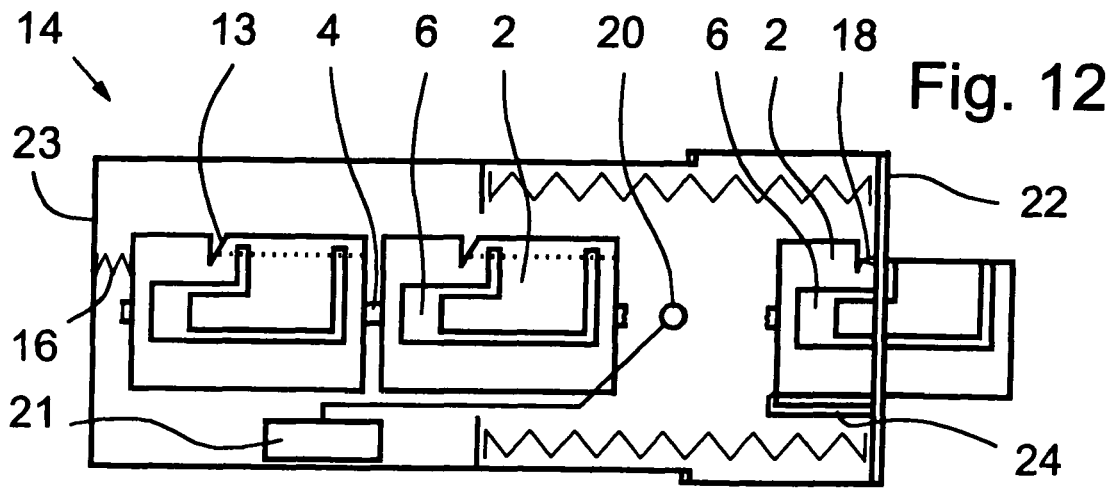
FIG. 12 shows the measuring instrument according to the second embodiment after studying the sample liquid when a used platform is being ejected.

FIGS. 10 to 12 show the device 1 with a plurality of platforms 2 according to a fourth embodiment with an assigned second embodiment of the measuring instrument 14.

The platforms 2 here are again attached directly to one another, but preferably by way of comparatively thin or highly weakened connections 4. If necessary, the platforms 2 can be located additionally on a carrier 10 for stabilization and/or can be provided with a continuous or common covering 8 for stabilization. However, the covering 8 (not shown in FIGS. 10 to 12), if necessary, may also be discontinuous, being provided only on the individual platforms 2.

It should be noted that, depending on the construction and structure of the platforms 2, optionally, also a subsequently applied covering 8 can be completely omitted. However, the execution of the cavities which are open to one flat side allows very simple production and especially, if necessary, also prior addition of reagents to the sample chamber 6; in that case, the covering 8 is necessary for sealing the platforms 2.

In the fourth embodiment the sample chamber 6 is located in the part of the respective platform 2 which is the rear part in the conveyance direction of the platforms 2. The channels 5, 7 end blindly, preferably, in the lateral edge area of the respective platform 2.

The measuring instrument 14 according to the second embodiment has two housing parts 22, 23 which can be moved toward one another or pushed into one another especially against spring force. Proceeding from the embodiment which is shown in FIG. 10, the front part 22 can be moved to the left—therefore relative to the platform 2 which is to be used next. Here, movement or actuation is possible using an opening means 18 which is formed in the illustrated example especially by a cutting edge, blade, scissors or the like in order to cut off the edge of the platform 2 such that at least the take-up channel 5 and preferably also the vent channel 7 are opened.

In the illustrated embodiment, the separation or cutting takes place in the lengthwise direction, i.e., in the conveyance direction of the platform 2 or in the direction of the lengthwise extension of the device 1. In particular, during opening, one edge strip is separated as far as a taper or undercut 13, the channels 5, 7, which cross the intersection line necessarily being opened.

In the opened state, which is shown in FIG. 11, the cut-off platform 2 projects especially with the take-up channel 5, such that, at this point, the sample liquid 3 can be taken up. The taken-up sample liquid 3 then flows into the sample chamber 6 which, in the illustrated embodiment, lies preferably in the area of the end of the platform 2 which is still in the measuring instrument 14 in order to enable the desired study or manipulation, preferably in turn with a suitable measurement means 20. The determined value can, in turn, be displayed by way of a display means 21.

After completed measurement, the used platform 2 is separated from the other platforms 2. In the illustrated example, the front part 22 is moved, for example, by releasing a catch (not shown) and preferably, spring force, again in the opposite direction, to the right in FIG. 11, the used platform 2 being entrained forward by a corresponding driver 24, therefore in the direction of motion, and in doing so, is separated from the other platforms 2 which are held back, for example, by a retaining means (not shown). The used platform 2 can then be removed or optionally directly ejected.

Finally, the unused platforms 2 can continue to be conveyed by the conveyor means or advance means 16, which is shown only very schematically in FIGS. 10 to 12, by a spring, for example, after release of a catch, so that the next platform 2 is moved forward into the initial position as shown in FIG. 10, and optionally, even causes the aforementioned ejection of the used platform 2.

Figure 13:
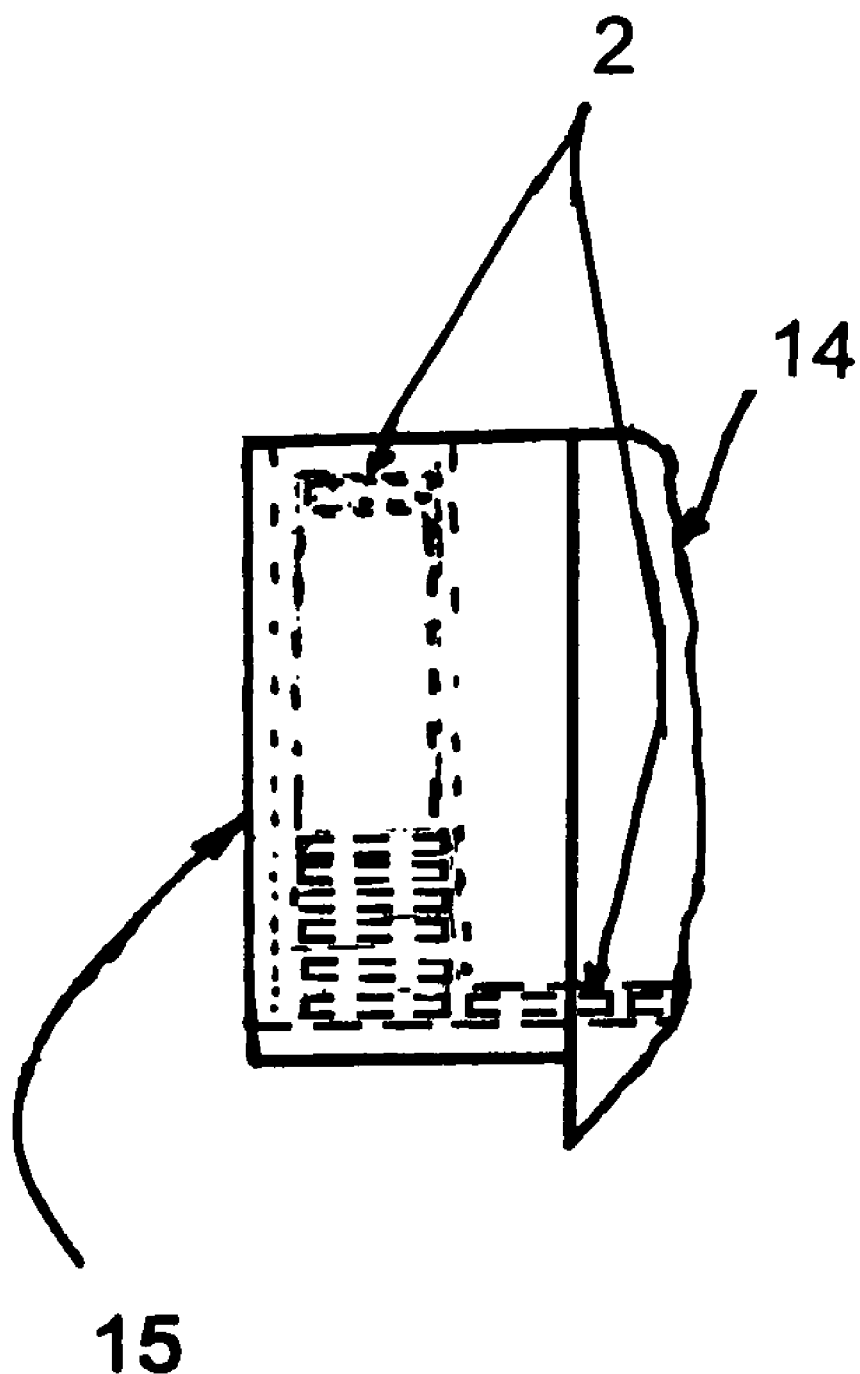
FIG. 13 shows a measuring instrument using a stacked arrangement of platforms.

FIG. 13 shows an interchangeable magazine 15 for use with measuring instrument 14 of FIGS. 10 to 12. The interchangeable magazine 15 contains a series of stacked platforms and to facilitate pulling out of the platforms, the connections 4 are formed of a connecting strip that has a length greater than that of each platform, is attached to each platform only at the trailing end (left in FIG. 13) and is folded-over between successive pairs of platforms. Each strip unfolds as the bottom-most platform of the pair is drawn out of the magazine so as to full underlie the trailing platform of the pair as the trailing platform becomes the bottom-most platform of the stack. The fact that the connecting strip is slightly longer than the platforms allows for spacing shown in FIGS. 10 to 12 to be formed.

The individual aspects and components of the described embodiments can be combined as required. Furthermore, a plurality of different designs which work according to the same basic principle are possible, especially kinematic reversals also being easily possible.

What is claimed is:

1. Device for taking-up and studying or manipulating a sample liquid, comprising:

a plurality of microfluidic platforms connected together in an end-to-end longitudinal series, each of the platforms having a sample chamber, a take-up channel with an open end connected to the sample chamber for taking up sample liquid contained therein and a closed end in an adjoining platform, and a vent channel with an open end connected to the sample chamber for venting thereof a closed end in the adjoining platform; and a separation line having means for separation of each individual platform from each adjoining platform, said means for separation being located between the open and closed ends of the take-up channel and of the vent channel such that said means for separation inherently also constitutes a means for opening the take-up and vent channels upon separation of each individual platform from each adjoining platform.

2. Device according to claim 1, wherein the connections of the platforms are frangible connections.

3. Device according to claim 1, wherein the platforms are covered by a continuous covering.

4. Device according to claim 3, wherein the covering covers at least one of a take-up channel for taking up the sample liquid and a vent channel of the platforms.

5. Device according to claim 3, wherein the covering also covers a sample chamber of the platforms.

6. Device according to claim 3, wherein the covering is made of a film.

7. Device according to claim 1, wherein the platforms are arranged in succession in a belt-shaped arrangement.

8. Device according to claim 1, wherein the plurality of microfluidic platforms are located on a belt-shaped common carrier.

9. Device according to claim 1, wherein the plurality of microfluidic platforms are located on a carrier made of a film.

10. Device according to claim 1, wherein the connected platforms are wound into a coil from which individual platforms are removable.

11. Device according to claim 1, wherein the connected platforms are arranged in a stack from which individual platforms are removable.

12. Device according to claim 1, wherein the platforms are provided with at least one of mechanical and optical markings, recesses, holes, tapers, weakenings, notches for enabling or facilitating at least one of conveyance, positioning, grasping and separation of individual platforms.

13. Microfluidic platform assembly, comprising:

a plurality of microfluidic platforms for taking-up and studying or manipulating a sample liquid, the platforms, in a sealed state, being covered by a common or continuous covering, said covering having a removable strip which covers an opening of a take-up channel for taking up the sample and an opening of a vent channel of each platform, wherein each of the platforms has means for being individually separated from an adjoining platform in a trasverse of the platform without opengin of said channels and means for individually removing at least a portion of said removable strip in a lengthwise direction of the platform so that both of said channels are opened thereby.

* * * * *